US009132159B2

(12) United States Patent
Nakamoto et al.

(10) Patent No.: US 9,132,159 B2
(45) Date of Patent: Sep. 15, 2015

(54) COMPOSITION FOR PREVENTION AND/OR TREATMENT OF TUMORS CONTAINING ACACIA DERIVATIVE

(75) Inventors: Yusho Nakamoto, Hatsukaichi (JP); Keiko Ono, Hatsukaichi (JP)

(73) Assignee: MIMOZAX CO., LTD., Hatsukaichi-shi (JP)

( * ) Notice: Subject to any disclaimer, the term of this patent is extended or adjusted under 35 U.S.C. 154(b) by 54 days.

(21) Appl. No.: 12/376,904

(22) PCT Filed: Aug. 10, 2006

(86) PCT No.: PCT/JP2006/315867
§ 371 (c)(1),
(2), (4) Date: Feb. 9, 2009

(87) PCT Pub. No.: WO2008/018140
PCT Pub. Date: Feb. 14, 2008

(65) Prior Publication Data
US 2010/0137423 A1    Jun. 3, 2010

(51) Int. Cl.
A61K 31/353    (2006.01)
A61P 39/06     (2006.01)
A61K 36/48     (2006.01)
A23K 1/16      (2006.01)
A23L 1/30      (2006.01)
C07D 311/62    (2006.01)

(52) U.S. Cl.
CPC ............... *A61K 36/48* (2013.01); *A23K 1/1646* (2013.01); *A23L 1/3002* (2013.01); *A61K 31/353* (2013.01); *C07D 311/62* (2013.01)

(58) Field of Classification Search
None
See application file for complete search history.

(56) References Cited

U.S. PATENT DOCUMENTS

| | | | |
|---|---|---|---|
| 5,629,338 A | 5/1997 | Okuda et al. | |
| 6,290,993 B1 | 9/2001 | Anderson et al. | |
| 6,294,190 B1 | 9/2001 | Nakahara et al. | |
| 7,514,469 B2 | 4/2009 | Jia | |
| 2003/0054055 A1* | 3/2003 | Nakamoto et al. | 424/770 |
| 2003/0180402 A1* | 9/2003 | Jia et al. | 424/757 |
| 2003/0230653 A1* | 12/2003 | Nakamoto et al. | 241/24.1 |
| 2003/0232099 A1 | 12/2003 | Pan et al. | |
| 2004/0186062 A1 | 9/2004 | Burnett et al. | |
| 2005/0058722 A1 | 3/2005 | Managoli | |
| 2005/0095332 A1 | 5/2005 | Stanley | |
| 2006/0204599 A1 | 9/2006 | Wheat | |
| 2008/0124415 A1 | 5/2008 | Tanaka et al. | |

FOREIGN PATENT DOCUMENTS

| | | |
|---|---|---|
| CN | 1753681 A | 3/2006 |
| FR | 2 710 533 A1 | 4/1995 |
| JP | 64-025726 | 1/1989 |
| JP | 3-287507 A | 12/1991 |
| JP | 6065074 A | 3/1994 |
| JP | 7-138178 A | 5/1995 |
| JP | 7300422 A | 11/1995 |
| JP | 8-259557 A | 10/1996 |
| JP | 9-291039 A | 11/1997 |
| JP | 10025238 A | 1/1998 |
| JP | 11-005975 | 1/1999 |
| JP | 11-180888 A | 7/1999 |
| JP | 2000-044472 A | 2/2000 |
| JP | 2000-073056 A | 3/2000 |
| JP | 2001-064172 | 3/2001 |
| JP | 2001098264 A | 4/2001 |
| JP | 2002-010753 A | 1/2002 |
| JP | 2002-051735 A | 2/2002 |
| JP | 2002-275076 A | 9/2002 |
| JP | 2003-519092 A | 6/2003 |
| JP | 2003-313138 A | 11/2003 |
| JP | 2003-342185 A | 12/2003 |
| JP | 2004-024054 A | 1/2004 |
| JP | 2004008215 A | 1/2004 |
| JP | 2004-051513 A | 2/2004 |
| JP | 2004-075579 A | 3/2004 |
| JP | 2004-091464 A | 3/2004 |
| JP | 2004-217559 A | 8/2004 |
| JP | 2004-300117 A | 10/2004 |
| JP | 2004532811 T | 10/2004 |
| JP | 2004-323362 A | 11/2004 |
| JP | 2004352639 A | 12/2004 |
| JP | 2005-068081 | 3/2005 |
| JP | 2005-521715 A | 7/2005 |
| JP | 2005-239559 A | 9/2005 |
| JP | 2005-529898 A | 10/2005 |
| JP | 2006-232781 A | 9/2006 |
| JP | 2006-232782 A | 9/2006 |
| WO | WO-03/082312 A1 | 10/2003 |
| WO | WO 03-092599 A2 | 11/2003 |
| WO | WO 2005/020932 A2 | 3/2005 |
| WO | WO 2006-003909 A1 | 1/2006 |

OTHER PUBLICATIONS

"Condensed tannins from steamed *Acacia mearnsii* bark" by Duan et al., Holzforschung 59, 289-94 (2005).*
"Antioxidant Activity of Extracts from *Acacia confusa* Bark and Heartwood" by Chang et al., J. Argic. Food Chem. 49, 3420-24 (2001).*
"Dietary Antioxidants in Health and Disease" by Morrissey et al., Int. Dairy J. 8, 463-72 (1998).*
"Dietary Intake and Bioavailability of Polyphenols" by Scalbert et al., J. Nutr. 130, 2073S-85S (2000).*
"The Molecular Biology of the Cell" by Alberts et al., Garland Publishing (New York), p. 725 (1994).*
Ohara "Chemical Properties and Application Development of Bark Tannin", APAST, vol. 13, No. 1 (Jan. 2003) pp. 7-11 (and English Translation, pp. 1-10).
Ohara et al., "Condensed Tannins from *Acacia mearnsii* and Their Biological Activities", Mokuzai Gakkaishi, 1994, vol. 40, No. 12, pp. 1363-1374.

(Continued)

*Primary Examiner* — Theodore R West
(74) *Attorney, Agent, or Firm* — Birch, Stewart, Kolasch & Birch, LLP

(57) ABSTRACT

It is intended to provide a composition which demonstrates an excellent antioxidative action in the body. The composition is an antioxidative composition containing an *acacia* bark derivative.

10 Claims, No Drawings

(56) References Cited

OTHER PUBLICATIONS

Ohara et al., "Juhi Tannin no Kagaku Tokusei to Yoto Kaihatsu", APAST, 2003, vol. 13, No. 1, pp. 7-11.

Takagi et al., "Tyrosinase Inhibitory Activity of Proanthocyanidins from Woody Plants", J. Wood Sci, 2003, vol. 49, No. 5, pp. 461-465.

Haridas et al., "Avicins: Triterpenoid saponins from *Acacia victoriae* (Bentham) induce apoptosis by mitochondrial perturbation" PNAS May 8, 2001, vol. 98, No. 10, pp. 5821-5826.

Extended European Search Report issued Feb. 17, 2012, in European Patent Application No. 06782653.7.

Yao et al., "The potential of wattle tannin extracts for fine use," Natural Product Research (Mar. 2006), vol. 20, No. 3, pp. 271-278.

African Territories Wattle Industry Fund Limited, Properties, Composition, Reactions and Industrial Applications of Mimosa Extract, Jan. 1980. pp. 2-10.

Botha et al., "Condensed tannins: direct synthesis, structure, and absolute configuration of four biflavonoids from black wattle bark ('mimosa') extract," J Chem Soc, Chem Commun, 1978, vol. 16, pp. 700-702.

Byers, "What can randomized controlled trials tell us about nutrition and cancer prevention?" CA Cancer J Clin, Nov.-Dec. 1999, vol. 49, No. 6, pp. 353-361.

Cheng et al., "A novel approach to microcalcification detection using fuzzy logic technique," IEEE Trans Med Imaging, Jun. 1998, vol. 17, No. 3, pp. 442-450.

Fragrance Journal, 1995, 23(10), pp. 96-102 (with English language abstract).

Garewal et al., "Clinical experience with the micronucleus assay," J Cell Biochem Suppl, 1993, vol. 52, No. 17F, pp. 206-212.

Granziero et al., "Adoptive immunotherapy prevents prostate cancer in a transgenic animal model," Eur J Immunol, Apr. 1999, vol. 29, No. 4, pp. 1127-1138.

http://www.merck.com/mmhe/sec15/ch180/ch180c.html, downloaded Apr. 14, 2009, "Risk Factors for Cancer," last review/revision Aug. 2008 by Bruce A. Chabner, MD; Elizabeth Chabner Thompson, MD, MPH.

http://www.merckmanuals.com/home/sec15/ch180/ch180a.html?qt=cancer&alt=sh, downloaded Dec. 4, 2010, "Overview of Cancer: Merck Manual Home Edition," last full review/revision Aug. 2008 by Bruce A. Chabner, MD; Elizabeth Chabner Thompson, MD, MPH.

Ishida et al., "Solid sampling technique for direct detection of condensed tannins in bark by matrix-assisted laser desorption/ionization mass spectrometry," Rapid Commun Mass Spectrom, 2005, vol. 19, No. 5, pp. 706-710.

Jacobus et al., Condensed Tannins: Direct Sysnthesis, Structure and Absolute Configuration of Four Biflavonoids from Black, Wattle (*Acacia mearnsii*) Bark, J.C. Chem. Comm. 1978. http://pubs.rsc.org/en/content/articlepdf/1978/c3/c39780000700.

Japanese Office Action issued in Japanese Patent Application No. 2005-132746 on Aug. 2, 2011, with English translation.

Japanese Office Action issued in JP 2005-132745 on Sep. 13, 2011, with English translation.

Kaur; "Antimutagenicity of ether and ethyl acetate fractionsn of *Acacia nilotica* in Ames assay", Breast, vol. 12, No. Supplement, (2003) p. s47.

Kronborg O., "Population screening for colorectal cancer, the goals and means," Ann Med, Oct. 1991, vol. 23, No. 4, pp. 373-379.

Liu et al., "Antidiabetic effect of Pycnogenol French maritime pine bark extract in patients with diabetes type II," Life Sci, Oct. 8, 2004, vol. 75, No. 21, pp. 2505-2513.

Orwa et al., "*Acacia mearnsii*, black wattle", Agroforestry Database 4.0 (2009) pp. 1-5.

Prakash et al., "Characterisation of Tannin from Indian Wattle (*Acacia mearnsii*) Bark," Indian Journal of Forestry, 1991, vol. 14, No. 4, pp. 299-302.

Properties, Composition, Reactions and Industrial Applications of Mimosa Extract, African Territories Wattle Industry Fund Limited, Jan. 1980, London, England.

Roux, "The Biogenesis of Bark and Heartwood Tannins of Some *Acacia* spp. and Their Taxonomic Significance," South African Journal of Science, 1962, vol. 58, No. 12, pp. 389-392.

Seigler, "Phytochemistry of *Acacia*-sensu lato," Biochemical Systematics and Ecology, 2003, vol. 31, No. 8, pp. 845-873.

Seiji Ohara, "Juhi Tannin no Kagaku Tokusei to Yoto Kaihatsu." APAST, 2003, vol. 13, No. 1, pp. 7-11.

Taguchi et al., "Evaluation of antipruritic effect of apple polyphenols using a new animal model of pruritus." J. Tokyo Med. Univ., Feb. 15, 2002, vol. 60, No. 2, pp. 123-129.

Tomatis, "Environmental cancer risk factors. A review." Acta Oncol, 1988, vol. 27, No. 5, pp. 465-472.

U.S. Office Action issued in U.S. Appl. No. 12/376,905 on Jan. 3, 2011.

U.S. Office Action issued in U.S. Appl. No. 12/376,905 on Oct. 20, 2010.

U.S. Office Action issued in U.S. Appl. No. 12/376,895 on Jan. 6, 2011.

U.S. Office Action issued in U.S. Appl. No. 12/376,895 on May 2, 2011.

U.S. Office Action issued in U.S. Appl. No. 12/376,895 on Nov. 2, 2010.

U.S. Office Action issued in U.S. Appl. No. 12/376,902 on Jan. 3, 2011.

U.S. Office Action issued in U.S. Appl. No. 12/376,902 on Jun. 15, 2011.

U.S. Office Action issued in U.S. Appl. No. 12/376,902 on Oct. 20, 2010.

U.S. Office Action issued in U.S. Appl. No. 12/376,905 on Jun. 15, 2011.

U.S. Office Action issued in U.S. Appl. No. 12/376,939 on Jan. 10, 2011.

U.S. Office Action issued in U.S. Appl. No. 12/376,939 on Jul. 21, 2011.

U.S. Office Action issued in U.S. Appl. No. 12/376,939 on Oct. 7, 2010.

Wassel et al., "Phytochemical examination and biological studies of *Acacia nilotica* L. Willd and *Acacia farnesiana* L. Willd growing in Egypt," Egyptian Journal of Pharmaceutical Sciences, 1992, vol. 33, Nos. 1-2, pp. 327-340.

* cited by examiner

COMPOSITION FOR PREVENTION AND/OR TREATMENT OF TUMORS CONTAINING ACACIA DERIVATIVE

TECHNICAL FIELD

The present invention relates to an antioxidative composition derived from a tree belonging to the genus *Acacia*, and to uses of this antioxidative composition as a food, an animal feed material, a medicine and a quasi-drug.

BACKGROUND ART

Oxygen is typically a stable substance referred to as triplet oxygen in the atmosphere. If a portion of that oxygen changes to a highly reactive substance referred to as active oxygen such as superoxide, hydroxy radical, singlet oxygen or hydrogen peroxide in the body, a portion of the substance fulfills the role of a biodefense mechanism against foreign substances produced by neutrophils and macrophages, while on the other hand, if the active oxygen is present in excess in the body, it has been clearly demonstrated to attack lipids, proteins, enzymes, nucleic acids or the like, resulting in damage to biomembranes, tissues and the like and causing arteriosclerosis, cerebrovascular disorders, pulmonary emphysema, rheumatoid arthritis, cataract, hypertension, senile dementia, Alzheimer's disease, or the occurrence of blotches and freckles, aging or the like.

In order to prevent the above various conditions caused by oxidative stress attributable to this excess active oxygen, a wide range of searches have been made for antioxidative substances whereby superoxide dismutase (SOD)-like substances having a function similar to that of SOD, which is an enzyme that catalyzes a reaction producing hydrogen peroxide and oxygen molecules by disproportionation of superoxide ($O_2^-$) that is a starting substance, and substances scavenging active oxygen (substances having active oxygen removing activity) are added to feeds.

For example, such substances include as a naturally-occurring substance liposoluble α-tocopherol (vitamin E) and water-soluble ascorbic acid (vitamin C), and as a synthetic substance phenolic substances such as butylhydroxytoluene (BHT), butylhydroxyanisole (BHA) and tertiary-butylhydroquinone (TBHQ).

However, although these substances are typically used as antioxidative substances in foods, their action in removing active oxygen from the body is inadequate and they have also been associated with problems, such as the synthetic substance, BHA, being suspected of possessing carcinogenicity.

Therefore, considerable research and development has been conducted in recent years to find an extremely safe active oxygen remover from natural sources such as animals and plants, and examples of such substances are disclosed in Patent Documents 1, 2, 3, 4 and 5. In addition, as for substances that have actually been commercialized, polyphenol-based compounds such as catechins extracted from tea leaves and cocoa bean extract, anthocyanin-based compounds contained in blueberry skin, and isoflavones obtained from fermented soy beans have attracted particular attention due to their extremely high level of active oxygen removal effects.

Among these polyphenol-based compounds that have been clearly demonstrated to have high active oxygen removal effects, catechins contained in tea leaves have been determined to demonstrate higher active oxygen removal effects than the other polyphenols, which catechins are flavanols having as a basic skeleton flavan-3-ol such as (−)epigallocatechin, (−)epigallocatechin-3-gallate, (−) epicatechin, (−)epicatechin-3-gallate and (+)catechin.

On the other hand, tannin, which is extracted with water from bark of an *Acacia* species, scientific name: *Acacia mearnsii* De Wild., has long been produced in large quantities in South Africa and Brazil. It is typically referred to as "wattle tannin", and is used inexpensively mainly as a tanning agent or in wood adhesives. In addition, since scientific name: *Acacia mangium* Willd. (*acacia mangium*) grows extremely rapidly, it has recently been planted extensively in subtropical and tropical regions such as in Indonesia and Malaysia. This wattle tannin is classified as a condensed tannin.

Recently, extracts of genus *Acacia* have been disclosed to have selective inhibitory effects on COX-2 (Patent Document 6), and bark of genus *Acacia* has been disclosed to have active oxygen removal effects (Patent Document 7) and skin whitening effects due to the effect of inhibiting tyrosinase activity (Patent Document 8).

However, bark of genus *Acacia* and polyphenols derived from bark thereof have not been known to be able to demonstrate an excellent antioxidative action in the body as a result of being ingested at a specific dose.

[Patent Document 1] JP01-25726A
[Patent Document 2] JP6-65074A
[Patent Document 3] JP7-300422A
[Patent Document 4] JP11-5975A
[Patent Document 5] JP2001-98264A
[Patent Document 6] JP2004-532811A
[Patent Document 7] JP2004-352639A
[Patent Document 8] JP10-025238A

DISCLOSURE OF THE INVENTION

Problems to be solved by the Invention

An object of the present invention is to provide a very safe composition which demonstrates an excellent antioxidative action in the body.

Means for Solving the Problems

As a result of conducting extensive studies to solve the above problems, the inventors of the present invention found that an excellent antioxidative action is demonstrated in the body by ingestion of an *acacia* bark derivative at a specific dose, thereby leading to the completion of the present invention.

Namely, the present invention relates to an antioxidative composition containing an *acacia* bark derivative(s) at a specific dose.

In addition, the present invention also relates to a method for preventing oxidation using an *acacia* bark derivative(s).

Moreover, the present invention also relates to a method for using an *acacia* bark derivative(s) for producing an antioxidative composition.

Effects of the Invention

According to the present invention, a composition can be provided that is able to demonstrate an excellent antioxidative action by being ingested at a specific dose.

In addition, the composition of the present invention is extremely safe and has less potential for adverse side effects and the like even if taken for a long period of time.

BEST MEANS FOR CARRYING OUT THE INVENTION

There are no particular limitations on the *acacia* bark derivative able to be used in the present invention provided that it is obtained by using as a raw material bark of a tree belonging to the genus *Acacia* (the tree is referred to as "*acacia*" or "genus *Acacia*" hereinafter), examples of which derivatives include a strip and a powder of *acacia* bark, and a suspension thereof, an extract such as a liquid extract, a concentrated liquid extract and a powdered extract of *acacia* bark, and a purified product obtained by purifying these extracts. The extract of *acacia* bark and particularly *acacia* bark polyphenols are preferable for production of excellent antioxidative activity.

In the present invention, only a single form of these *acacia* bark derivatives may be used, or alternatively two or more forms thereof may be used in combination.

Although there are no particular limitations on *acacia* able to be used in the present invention so long as it is a tree belonging to the genus *Acacia*, with respect to obtaining an *acacia* bark derivative having an excellent antioxidative action, bark of the genus *Acacia* selected from the group consisting of scientific name: *Acacia mearnsii* De Wild. (generic name: black wattle), scientific name: *Acacia mangium* Willd. (generic name: *Acacia mangium*), scientific name: *Acacia dealbata* Link, scientific name: *Acacia decurrens* Willd. and scientific name: *Acacia pycnantha* Benth. are preferable, while *Acacia mearnsii* De Wild. and *Acacia mangium* Willd. are particularly preferable.

In the present invention, only a single form of these *acacia* bark may be used, or alternatively two or more forms thereof may be used in combination.

The aforementioned *acacia* bark can normally be obtained by cutting down an *acacia* tree, pealing off only bark and then drying the bark more preferably by sun-drying.

Bark of *acacia* is comprised of an outer bark and a somewhat fibrous inner bark, and when dried to a moisture content of about 20% or less, can be easily finely pulverized in a size reducing mill such as a hammer mill. In the present invention, both the outer bark and inner bark of the genus *Acacia* may be used together or either one may be used alone as the *acacia* bark.

The aforementioned strip of *acacia* bark can be obtained in accordance with commonly used methods by pulverizing the *acacia* bark to a suitable size.

In addition, although the aforementioned powder of *acacia* bark can be obtained by pulverizing the *acacia* bark into a powder in accordance with commonly used methods, in particular, the particle diameter of the resulting powder is preferably 100 μm or less and particularly preferably 50 to 70 μm. Powder fractionation can be carried out by pulverizing the bark dried to a moisture content of 20% or less to a suitable size such as a particle diameter of about 1.6 mm or less, and then classifying the resulting powder with a vibrating screen or the like to obtain the required powder.

The aforementioned extract of *acacia* bark can be obtained by extraction from the *acacia* bark in accordance with commonly used methods. In order to obtain an extract of *acacia* bark having an excellent antioxidative action, it is preferably extracted from the *acacia* bark with an alcohol or a polar solvent.

Ethanol, etc. can be used as the alcohol, and water, etc. can be used as the polar solvent, and these solvents may be used singly or in combination of two or more kinds as necessary. A mixed solvent of water and the alcohol such as ethyl alcohol is particularly preferable for production of an excellent antioxidative action.

Moreover, the extraction procedure may be carried out a number of times using the same or different solvents.

In terms of obtaining an extract having an excellent antioxidative action, an extract which is obtained by extracting from the *acacia* bark with water or hot water, and then further extracting from the resulting extract with ethanol may be used.

Although the extraction is carried out by adding the solvent to a strip, a powder or the like of the *acacia* bark followed by stirring as necessary, there are no particular limitations on temperature, time or solid-liquid ratio. In the case of using water as the solvent, the extraction may also be carried out with hot water. The resulting liquid extract may be freeze-dried or spray-dried directly, or may be freeze-dried or spray-dried after concentrating under reduced pressure. The resulting extract can be in various forms, such as a liquid extract, solution, powder, concentrate or paste, and can be used in a wide range of forms as necessary.

Moreover, the *acacia* bark extract of the present invention obtained in any of these forms can be used directly as an antioxidative composition, or a purified product obtained by purifying the extract as necessary can also be used as an antioxidative ingredient.

In the present invention, ingredients contained in bark of the genus *Acacia* are also examples of the *acacia* bark derivatives. Examples of such ingredients are the *acacia* bark polyphenols. The *acacia* bark polyphenols are particularly preferable ingredients since they produce excellent antioxidative action.

The *acacia* bark polyphenols of the present invention refer to a type of condensed tannins in the form of polymers in which flavanols having as a basic skeleton flavan-3-ol such as (−)-fisetinidol, (−)-robinetinidol, (+)-catechin and (+)-gallocatechin are linked by C4-C8 or C4-C6 bonds. Here, the molecular weights of such condensed tannins are preferably 300 to 3000 and particularly preferably 500 to 3000. The *acacia* bark polyphenols used in the present invention can be obtained by extracting from the powder, etc. of the *acacia* bark with hot water as previously described.

In addition, examples of commercially available *acacia* bark polyphenols include MIMOSA ME POWDER, MIMOSA MS POWDER, MIMOSA GS POWDER, MIMOSA FS POWDER, MIMOSA WS POWDER, MIMOSA RG POWDER, MIMOSA RN POWDER, MIMOSA DK POWDER, MIMOSA AL POWDER, MIMOSA CR POWDER and GOLDEN MIMOSA POWDER (all registered trademarks) which are manufactured by Mimosa Central Co-operative Ltd., and the like.

Although the composition of the present invention may be the *acacia* bark derivative(s) such as the *acacia* bark, the extract(s) thereof, the purified product(s) thereof or the *acacia* bark polyphenol(s) per se, it may also contain other substance(s) having an antioxidative action, such as vitamin C, vitamin E, coenzyme Q10, α-tocopherol, proanthocyanin, isoflavone, quercetin, green tea or wheat germ. Coenzyme Q10, green tea or wheat germ are particularly preferably contained since they produce excellent antioxidative actions due to synergistic effects.

Although the composition of the present invention may be the *acacia* bark derivative(s) such as the *acacia* bark, the extract(s) thereof, the purified product(s) thereof or the *acacia* bark polyphenol(s) per se, it may contain vehicles, sweeteners, sour flavorings, thickeners, fragrances, pigments, emulsifiers, and other additives or materials which are ordinarily used in drug formulations or foods, so long as they do not undermine the effects of the present invention.

The composition of the present invention can be used to prevent or treat diseases associated with active oxygen. In the present invention, there are no particular limitations on the diseases associated with active oxygen provided they are cellular or tissue disorders caused by active oxygen such as superoxide, hydroxy radicals, singlet oxygen or hydrogen peroxide, or by lipid peroxides and the like oxidized by them. Examples of the diseases reported include arteriosclerosis, cerebrovascular disorders, pulmonary emphysema, rheumatoid arthritis, cataract, hypertension, senile dementia, Alzheimer's disease, or blotches and freckles or aging, while a good example is arteriosclerosis.

There are no particular limitations on an ingested amount of the composition according to the present invention, and the ingested amount can be suitably selected depending on the dosage form as well as the age, body weight and symptoms of an ingesting person such as a user or patient, or an ingesting animal. For example, the composition has an excellent anti-oxidative action by being ingested, in particular orally ingested at an amount of the *acacia* bark polyphenol(s) ranging from 0.001 to 1 g, preferably from 0.001 to 0.5 g and more preferably form 0.005 to 0.1 g per 1 kg of body weight of the ingesting person or ingesting animal per day in terms of the amount of an active ingredient.

The duration of ingestion can be arbitrarily determined depending on the age and symptoms of the ingesting person or ingesting animal.

The composition according to the present invention can be used as a food or an animal feed material such as a health food, a functional food, a health supplement food, a food for specified health use, a beauty food or a nutritional supplement food (supplement). For example, these foods and animal feed material may also be in the form of a beverage such as tea or juice; ice cream, jelly, candy, chocolate or chewing gum, etc. In addition, they may also be in the form of liquids, powders, granules, capsules or tablets. Here, animals fed by the animal feed material include all animals requiring the prevention or treatment of diseases associated with active oxygen as listed above, including pets, livestock or animals bred at zoos, etc.

In addition, although the composition according to the present invention can be administered as a medicine or a quasi-drug, for example, orally in the form of powders, tablets, coated tablets, sugar coated pills, hard or soft gelatin capsules, liquids, emulsions or suspensions, it can also be administered parenterally, such as rectally in the form of suppositories, or such as locally or percutaneously in the form of ointments, creams, gels or liquids.

EXAMPLES

Although the following provides a more detailed explanation of the present invention through production examples, test examples and formulation examples thereof, the present invention is not limited thereto. In particular, although the following examples are indicated without making a distinction between the outer bark and inner bark of the *acacia* bark of the present invention, the outer bark can be separated from the inner bark and each can also be used, separately.

In the following production examples, test examples and the like, each *acacia* of the present invention is indicated with numbers shown in parentheses after each scientific name. For example, *acacia* known by the scientific name of *Acacia mearnsii* De Wild. is indicated as *Acacia* No. 1.

Scientific name: *Acacia mearnsii* De Wild. (No. 1), scientific name: *Acacia mangium* Willd. (No. 2), scientific name: *Acacia dealbata* Link (No. 3), scientific name: *Acacia decurrens* Willd. (No. 4), scientific name: *Acacia pycnantha* Benth. (No. 5).

In addition, percentages (%) refer to percent by weight (wt %) unless specifically indicated otherwise.

Production Example 1

*Acacia* Bark Powder

Bark of *Acacia* No. 1 was dried to a moisture content of 20% or less and after pulverizing the dried bark in a hammer mill to a powder having a particle diameter of 1.6 mm or less (the powder passing through a 10 mesh Tyler screen), the powder was further classified with a vibrating screen to obtain a fine powder having a particle diameter of 63 µm or less (passing through a 250 mesh screen).

Fine powders each having a particle diameter of 63 µm or less were similarly obtained by pulverizing bark of the remaining four types of *acacia* namely *Acacia* No. 2 to *Acacia* No. 5. Although there were some differences in the efficiency by which the fine powder passed through the 250 mesh screen depending on the type, all of the target fine powders were able to be obtained.

Production Example 2

*Acacia* Bark Extract

Bark of each *Acacia* No. 1 to 5 of the present invention was dried to a moisture content of 20% or less and after pulverizing the dried bark in a hammer mill to a powder having a particle diameter of 1.6 mm or less, five times the amount of hot water were added to 100 g of the dried pulverized bark followed by extraction for 15 minutes after boiling, and then filtering using a 10 to 20 µm filter. The resulting filtrate was spray-dried in a spray dryer to obtain 40 g of each bark extract.

The bark extracts are hereinafter indicated as *Acacia* Hot Water Extracts Nos. 1 to 5, respectively.

Production Example 3

*Acacia* Bark Extract

*Acacia* bark of the present invention was dried to a moisture content of 20% or less and after pulverizing the dried bark in a hammer mill to a powder having a particle diameter of 1.6 mm or less, five times the amount of ethanol were added to 100 g of the dried pulverized bark followed by extraction for 15 minutes while refluxing after boiling, and then filtering using a 10 to 20 µm filter. After evaporating the ethanol from the resulting filtrate, the concentrate was spray-dried in a closed spray dryer to obtain 40 g of bark extract (to be indicated hereinafter in the manner of *Acacia* Ethanol Extract No. 1).

*Acacia* Ethanol Extracts Nos. 1 to 5 were obtained in the same manner.

Production Example 4

*Acacia* Bark Extract

Three times the amount of ethanol were added to 10 g of the *acacia* hot water extract obtained in Production Example 2 followed by extraction for 15 minutes while refluxing after boiling, and then filtering using a 10 to 20 µm filter. The ethanol was evaporated from the resulting filtrate, water was added thereto, and then freeze-dried to obtain 9 g of extract (to be indicated hereinafter in the manner of *Acacia* Hot Water Extract Ethanol Fraction No. 1).

*Acacia* Hot Water Extract Ethanol fractions Nos. 1 to 5 were obtained in the same manner.

Test Example 1

Antioxidation Test (1)

(1) Test Method

*Acacia* Hot Water Extract No. 1 described in Production Example 2 was suspended in 0.3% (w/v) sodium carboxymethyl cellulose solution (CMC-Na solution) and orally administered for 14 days to rats (Slc:SDF, males, age 7 weeks) at a daily dose of 2 g/kg. CMC-Na solution was administered to a control group.

The concentrations of 8-hydroxy-2'-deoxyguanosine (8-OHdG) in the serum and urine of the rats were measured on day 14 after the start of administration using High-Sensitivity 8-OHdG Check and New 8-OHdG Check, respectively (Nikken Seil Co., Ltd.).

Each of the measured values was expressed in the form of the mean±standard error. Testing for the presence of a significant difference from the control group was carried out using the Student's t-test. The level of significance was indicated as 5%.

(2) Test Results

The results are shown in Table 1. None of the rats died or demonstrated abnormalities in general condition.

TABLE 1

Changes in 8-OHdG Concentrations

| Dose group | No. of animals | 8-OHdG concentration (ng/mL) | |
| --- | --- | --- | --- |
| | | Serum | Urine |
| Control group | 8 | 0.010 ± 0.007 | 46.474 ± 5.947 |
| Test group | 8 | 0.009 ± 0.006 (10.00%) | 22.712 ± 7.084* (51.13%) |

( ): Indicates rate of decrease (%) versus control group
*Comparison with control group. It shows P < 0.05.

Test Example 2

Antioxidation Test (2)

(1) Preparation of Test Sample Solutions

*Acacia* Hot Water Extract No. 1 described in Production Example 2, which was prepared in the same manner as Test Example 1, was orally administered for 14 days to rats (Slc: SD, males, age 7 weeks) at a daily dose of 0.1 to 2.0 g/kg. The CMC-Na solution was administered to a control group.

The concentrations of 8-OHdG in urine were measured in the same manner as the aforementioned Test Example 1 on day 14 after the start of administration.

The measured values were expressed in the form of the mean±standard deviation. Testing for the presence of a significant difference between each dose group and the control group was carried out using Dunnett's multiple comparison test. The level of significance was indicated as 5% or 1%.

(2) Test Results

The results are shown in the following Table 2. None of the rats died or demonstrated abnormalities in general condition.

TABLE 2

Urine Concentrations of 8-OHdG.

| Dose group | No. of animals | 8-OHdG concentration (ng/mL) |
| --- | --- | --- |
| Control group | 8 | 31.224 ± 5.367 |
| Acacia Hot Water Extract No. 1 | | |
| 0.1 g/kg dose group | 8 | 31.311 ± 16.507 (−0.28%) |
| 0.5 g/kg dose group | 8 | 27.341 ± 9.424 (12.44%) |
| 2.0 g/kg dose group | 8 | 25.554 ± 11.980 (18.16%) |

( ): Indicates rate of decrease (%) versus control group

On the basis of the results of Test Examples 1 and 2 above, the *acacia* bark polyphenols were clearly demonstrated to have an antioxidative action.

Test Example 3

Mutagenicity Test

A mutagenicity test was conducted in compliance with the Ministry of Health, Labor and Welfare Notification No. 77 (Sep. 1, 1988). As a result of testing with test substance (*Acacia* Hot Water Extracts Nos. 1 to 5 of Production Example 2) at doses of 156 to 5,000 µg/plate, there were no increases in the numbers of revertant colonies for any of the bacterial strains.

Test Example 4

Micronucleus Test

The presence of the ability to induce micronuclei was investigated in vivo in accordance with ordinary methods. *Acacia* Hot Water Extract No. 1 was orally administered twice at 24-hour intervals at daily doses of 2,000, 1,000 and 500 mg/kg to male ICR mice followed by the preparation of micronucleus specimens 24 hours after the final dosing.

*Acacia* Hot Water Extract No. 1 did not demonstrate positive results at any of the dose levels. In addition, there were no constant fluctuations in the simultaneously observed ratio of total polychromatic erythrocytes to total erythrocytes, and inhibition of erythrocyte proliferation was not observed in comparisons with a negative control group.

Test Example 5

Mouse Acute Toxicity Study (Oral Administration)

An acute oral dose toxicity study was conducted using male and female ICR mice in compliance with OECD (Guidelines for the Testing of Chemicals, 401, 1987). As a result, the $LD_{50}$ value of *Acacia* Hot Water Extract No. 1 was 4,468 mg/kg among males and 3,594 mg/kg among females.

Similar results were obtained in the above study for *Acacia* Hot Water Extracts Nos. 2 to 5 of Production Example 2.

Test Example 6

Rat Repeated Dose Toxicity Study (Oral Administration)

A 13-week repeated dose toxicity study was conducted using rats in accordance with ordinary methods. Mixed feed containing 0.5, 1.5 and 5.0% of *Acacia* Hot Water Extract No. 1 was fed to male and female Slc:SD rats.

As a result, none of the rats died or demonstrated abnormalities in examinations, including general condition.

Test Example 7

Human Single Dose Study

Five healthy adult males age 32 to 43 years were given 1500 mg of *Acacia* Hot Water Extract No. 1 (12 tablets of Formulation Example 4 described below). Although general examinations, hematology tests, blood biochemistry tests and urinalyses were performed on the subjects before ingestion, 3 hours after ingestion, 8 hours after ingestion, 24 hours after ingestion and 1 week after ingestion, there were no clinically significant fluctuations in test values. There were also no adverse events attributable to the tablets.

Test Example 8

Human 4-Week Continuous Dosing Study

Twenty-five healthy adult males age 23 to 44 years were given *Acacia* Hot Water Extract No. 1 of Formulation Example 4 described below at 750 mg/day (6 tablets of Formulation Example 4) and 1000 mg/day (8 tablets of Formulation Example 4) for 4 weeks each.

General examinations, hematology tests and urinalyses were performed on the subjects of each group before ingestion, 2 weeks after ingestion, 4 weeks after ingestion and 2 weeks following completion of ingestion. There were no clinically significant fluctuations in test values. There were also no adverse events.

Formulation Example 1

Preparation of Internal Medication

An internal medication having the composition indicated below was prepared using the *acacia* bark Hot Water Extract Ethanol Fraction of Production Example 4.

| | |
|---|---|
| Extract fraction of Production Example 4 | 1.0 (wt %) |
| Lactose | 30.0 |
| Cornstarch | 60.0 |
| Crystalline cellulose | 8.0 |
| Polyvinyl pyrrolidone | 1.0 |
| Total | 100.0 |

Formulation Example 2

Preparation of Pet Food

A pet food having the composition indicated below was prepared using the *acacia* bark Hot Water Extract of Production Example 2.

| | |
|---|---|
| Extract of Production Example 2 | 1.0 (wt %) |
| Oatmeal | 88.0 |
| Starch | 5.0 |
| Salt | 2.5 |
| Whole egg | 3.0 |
| Flavoring | 0.5 |
| Total | 100.0 |

Formulation Example 3

Preparation of Tablets (Confections)

Tablets (confections) having the composition indicated below were prepared using the *acacia* bark Hot Water Extract Ethanol Fraction of Production Example 4.

| | |
|---|---|
| Extract fraction of Production Example 4 | 1.0 (wt %) |
| Citric acid | 1.0 |
| Powdered skim milk | 15.0 |
| Sucrose ester | 1.0 |
| Flavoring | 0.5 |
| Powdered sugar | 20.0 |
| Lactose | 61.5 |
| Total | 100.0 |

Formulation Example 4

Preparation of Tablets

Tablets having the composition indicated below were prepared using *Acacia* Bark Hot Water Extract No. 1 of Production Example 2.

| | |
|---|---|
| *Acacia* Bark Hot Water Extract No. 1 of Production Example 2 | 125 (mg) |
| Sucrose ester | 9 |
| Lactose | 166 |
| Total | 300 |

INDUSTRIAL APPLICABILITY

According to the present invention, a composition for the prevention and/or treatment of diseases associated with active oxygen can be obtained.

More specifically, the composition of the present invention is useful for preventing and/or treating arteriosclerosis.

The composition can be used in a medicine, a quasi-drug or a cosmetic, or a food or an animal feed material such as a health food, a health supplement food, a food for specified health use or a nutritional supplement food.

The invention claimed is:

1. A method of preventing or treating oxidation involving active oxygen in the body which comprises:
    orally administering to a person or animal in need thereof a composition comprising:
        a hot water extract(s) of *acacia* bark in an amount effective to remove active oxygen in the body thereby preventing or treating said oxidation; and
        at least one of food, animal feed, or medicine;
    wherein the *acacia* bark extract is prepared from bark from at least one of *Acacia mearnsii* De Wild., *Acacia mangium* Willd., *Acacia dealbata* Link, *Acacia decurrens* Willd. and *Acacia pycnantha* Benth;
    wherein the *acacia* bark extract comprises *acacia* bark polyphenol(s) and the composition is administered at a dose of 0.001 to 1 g *acacia* bark polyphenol(s) per 1 kg of body weight per day; and
    wherein the *acacia* bark polyphenol(s) is a condensed tannin(s), having a molecular weight(s) of 500 to 3000, and is a polymers) of flavanols having flavan-3-ol as a basic skeleton linked by C4-C8 or C4-C6 bonds, and said flavan-3-ol is selected from the group consisting of (−)fisetinidol, (−)-robinetinidol, (+)-catechin and (+)-gallocatechin.

2. The method of preventing or treating oxidation involving active oxygen in the body according to claim 1, wherein the *acacia* bark extract is prepared from a bark of *Acacia mearnsii* De Wild.

3. The method of preventing or treating oxidation involving active oxygen in the body according to claim 1, wherein the composition is orally administered at a dose of 0.005 to 1 g per kg of body weight per day in terms of the amount of active ingredient.

4. The method of preventing or treating oxidation involving active oxygen in the body according to claim 1, wherein the composition is added to a food and the administering comprises the person ingesting the food.

5. The method of preventing or treating oxidation involving active oxygen in the body according to claim 1, wherein the composition is added to an animal feed and the administering comprises the animal ingesting the animal feed.

6. The method of preventing or treating oxidation involving active oxygen in the body according to claim 1, wherein the composition is added to a medicine and the administering comprises the person or animal ingesting the medicine.

7. The method of preventing or treating oxidation involving active oxygen in the body according to claim 1, wherein said flavan-3-ol is (−)-robinetinidol or (+)-catechin.

8. The method of preventing or treating oxidation involving active oxygen in the body according to claim 1, wherein said person or animal has at least one of arteriosclerosis, cerebrovascular disorders, pulmonary emphysema, cataract, hypertension, senile dementia, Alzheimer's disease, and blotches.

9. A method of preventing or treating oxidation involving active oxygen in the body which comprises:
orally administering to a person or animal in need thereof at a dose of 0.001 to 1 g *acacia* bark polyphenol(s) per 1 kg of body weight per day, a composition consisting of:
  a hot water extract(s) of *acacia* bark in an amount effective to remove active oxygen in the body at in an amount to provide said dose of *acacia* bark polyphenol(s) and thereby prevent or treat said oxidation;
  at least one of food, animal feed, or medicine; and
  optionally at least one of vitamin C, vitamin E, coenzyme Q10, α-tocopherol, proanthocyanin, isoflavone, quercetin, green tea, and wheat germ;
wherein the *acacia* bark extract is prepared from bark from at least one of *Acacia mearnsii* De Wild., *Acacia mangium* Willd., *Acacia dealbata* Link, *Acacia decurrens* Willd. and *Acacia pycnantha* Benth; and
wherein the *acacia* bark polyphenol(s) is a condensed tannin(s), having a molecular weight(s) of 500 to 3000, and is a polymer(s) of flavanols having flavan-3-ol as a basic skeleton linked by C4-C8 or C4-C6 bonds, and said flavan-3-ol is selected from the group consisting of (−)fisetinidol, (−)-robinetinidol, (+)-catechin and (+)-gallocatechin.

10. The method of preventing or treating oxidation involving active oxygen in the body according to claim 9, wherein said person or animal has at least one of arteriosclerosis, cerebrovascular disorders, pulmonary emphysema, cataract, hypertension, senile dementia, Alzheimer's disease, and blotches.

* * * * *

UNITED STATES PATENT AND TRADEMARK OFFICE
CERTIFICATE OF CORRECTION

| | |
|---|---|
| PATENT NO. | : 9,132,159 B2 |
| APPLICATION NO. | : 12/376904 |
| DATED | : September 15, 2015 |
| INVENTOR(S) | : Yusho Nakamoto et al. |

Page 1 of 1

It is certified that error appears in the above-identified patent and that said Letters Patent is hereby corrected as shown below:

ON THE TITLE PAGE AND IN THE SPECIFICATION:

At item (54) and at Column 1, lines 1-3, change the title to read as follows:

--ANTIOXIDATIVE COMPOSITION CONTAINING ACACIA BARK DERIVATIVE--.

IN THE SPECIFICATION:

Column 5, line 24, change "form" to --from--.

IN THE CLAIMS:

In claim 1, at Column 10, line 66 (second line from the bottom), change "polymers)" to --polymer(s)--.

Signed and Sealed this
Nineteenth Day of July, 2016

Michelle K. Lee
*Director of the United States Patent and Trademark Office*